United States Patent [19]

Bernstein

[11] Patent Number: 4,590,212

[45] Date of Patent: May 20, 1986

[54] METHOD OF INCREASING THE RATE OF WOUND HEALING AND COMPOSITION

[75] Inventor: Joel E. Bernstein, Deerfield, Ill.

[73] Assignee: Soft Sheen Products, Inc., Chicago, Ill.

[21] Appl. No.: 328,904

[22] Filed: Dec. 9, 1981

[51] Int. Cl.$^4$ ............................................ A61K 31/16
[52] U.S. Cl. .................................................. 514/629
[58] Field of Search ....................... 424/324, 230, 234; 514/579, 629

[56] References Cited

U.S. PATENT DOCUMENTS 2,975,097  3/1961  Modderno et al. ................. 424/234
3,981,996  9/1976  Leigh ................................ 424/230

OTHER PUBLICATIONS

Merck Index, 6th ed. 1976, p. 6, #36.
*Handbook of Nonprescription Drugs,* 6th ed. Richard Penna, Am Phar. Assoc. 1979, pp. 137–140.

*Primary Examiner*—Jerome D. Goldberg
*Assistant Examiner*—John W. Rollins
*Attorney, Agent, or Firm*—Allegretti, Newitt, Witcoff & McAndrews, Ltd.

[57] ABSTRACT

A method of and composition for increasing the rate of healing of a wound wherein an effective amount of acetaminophen is applied in divided doses to the wound. The acetaminophen is present in an amount of not less than about 0.05 percent by weight of the carrier.

16 Claims, No Drawings

METHOD OF INCREASING THE RATE OF WOUND HEALING AND COMPOSITION

BACKGROUND OF THE INVENTION

Wounds of all sizes and shapes may result from a variety of accidental, surgical, and even self-inflicted insults to the skin and underlying tissues. Many factors are involved in wound healing including nutritional, hormonal and even psychological. Some patients who had undergone punch biopsies of the skin for diagnostic purposes had unusually rapid healing at the biopsy sites. In questioning several of such subjects, I learned that the only factor they had in common was their rather regular use of acetaminophen as an oral analgesic agent (for treatment of recurring headaches).

I prepared a number of topical preparations containing varying concentrations of acetaminophen ranging from 0.05 percent to 10 percent by weight of the carrier (vehicle) and applied these to wounds of various nature where the experimental subject had several such wounds so that the topical vehicle alone could be compared as control. Surprizingly, creams, ointments and solutions containing acetaminophen produced an apparent increase in the rate of healing of such wounds when compared to the carrier alone.

SUMMARY OF THE INVENTION

The present invention relates to a method of and composition for increasing the rate of wound healing in which acetaminophen is the principal active ingredient in a topical formulation.

An important object of the present invention is to provide a method of increasing the rate of healing of a wound comprising topically applying an effective amount of acetaminophen to the wound.

Another object of the present invention is to increase the rate of healing of a wound comprising topically applying an effective amount of acetaminophen in a pharmaceutically acceptable carrier to the wound.

A still further object of the present invention is to provide a method of increasing the rate of healing of a wound comprising topically applying a pharmaceutically acceptable carrier containing an effective amount of acetaminophen in divided doses to the wound.

Yet another object of the present invention is to provide a composition comprising a pharmaceutically acceptable carrier containing acetaminophen present in the range of from about 0.05 percent to about 10 percent by weight of the carrier.

DETAILED DESCRIPTION OF THE PREFERRED EMBODIMENT

In the practice of the present invention, acetaminophen is distributed according to known techniques in various pharmaceutically acceptable carriers such as emulsions, solutions, suspensions including lotions, creams and ointments. Some of these carriers such as the solutions may be acqueous carriers and some may contain volatile diluents such as alcohol, glycol and may also contain wetting agents, emulsifying and suspending agents.

Acetaminophen, the active ingredient in the wound healing formulation, is present in the range of from about 0.05 percent to about 10 percent by weight of the carrier and such preparations preferably are applied in divided doses to the wound, periodically from 1 to 8 times daily. Chemically, acetaminophen is the N-acetyl-p-aminophenol, the chemical formula of which is:

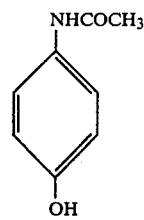

Acetaminophen is utilized in medical therapy as an anti-pyretic and analgesic. It is devoid of antiinflammatory or antirheumatic properties, wherefore additional therapeutical usages are unknown.

If the acetaminophen is present in an amount less than about 0.05 percent by weight, then there is insufficient concentrations of the acetaminophen to provide effective therapy. If the acetaminophen is present in an amount greater than about 10 percent by weight of the pharamceutically acceptable carrier, then the chemical reaction with respect to wound healing may be altered significantly. The acetaminophen is preferably administered topically in divided doses from about 1 to 8 times daily.

The following examples further illustrate the present invention:

EXAMPLE 1

1% acetaminophen was incorporated into U.S.P. cold cream and applied four times daily to an excoriated mosquito bite in an 11 year old male, while U.S.P. cold cream alone was applied to a contiguous excoriated mosquito bite. After three days, the scratch treated with the topical 1% acetaminophen had completely healed while it took an additional two days for the other excoriated bite to heal.

EXAMPLE 2

An aqueous alcohol solution containing 5% acetaminophen was applied four times daily to a skin biopsy site (3 mm) on the upper arm of a 39 year old patient while the vehicle alone was applied to a 3 mm biopsy site on the forearm. The acetaminophen treated site healed completely in 8 days while that treated with vehicle took 15 days to heal completely.

EXAMPLE 3

10% acetaminophen was incorporated into Eucerin ® cream and applied to an abrasion on the knee of a 6 year old and a similar abrasion on the opposite knee was treated with Eucerin ® alone. Both creams were applied 3-4 times daily. The abrasion on the knee receiving the acetaminophen applications healed within 4 days while the knee receiving plain Eucerin ® required 7 days to heal.

EXAMPLE 4

0.05% acetaminophen was incorporated into white petrolatum and applied to an abrasion on the skin of a 36 year old patient. The abrasion was completely healed within 3 days, an unusually short time for healing on the lower leg.

EXAMPLE 5

2% acetaminophen was incorporated into an alcoholic gel containing 6% polyoxyethylene lauryl ether and applied three times daily to 2 lacerations on the right foot of a 11 year old child. One laceration similar in size and depth was left untreated. The lacerations treated with the acetaminophen gel completely healed in 5 days while the untreated laceration healed in eight days.

EXAMPLE 6

A cream containing 6% acetaminophen was applied twice daily to the surgical incision site of a 74 year old patient who had recently undergone abdominal surgery and had a history of slow healing. No problems were encountered in wound healing and the incision site was completely healed within 9 weeks.

It will be apparent to those skilled in the art that only the preferred embodiments have been described by way of exemplification and that there are various modifications and alterations therein which fall within the scope of this invention and are intended to be covered in the claims appended hereto.

What is claimed is:

1. A method of increasing the rate of healing of a wound in a patient having a wound comprising topically applying to the wound an effective amount of acetaminophen to increase the rate of healing of the wound.

2. The method of claim 1, wherein the acetaminophen is applied in divided doses.

3. The method of claim 1, wherein the acetaminophen is applied in divided doses of from one to eight times daily.

4. A method of increasing the rate of healing of a wound in a patient having a wound comprising topically applying to the wound an effective amount of acetaminophen to increase the rate of healing of the wound, the acetaminophen being in a pharmaceutically acceptable carrier.

5. The method of claim 4, wherein the pharmaceutically acceptable carrier is an ointment or cream.

6. The method of claim 4, wherein the pharmaceutically acceptable carrier is an aqueous solution.

7. The method of claim 4, wherein the pharmaceutically acceptable carrier contains alcohol.

8. The method of claim 4, wherein the acetaminophen is present in the range of from about 0.05 percent to about 10 percent by weight of the carrier.

9. The method of claim 4, wherein the acetaminophen is present in the range of from about 0.05 percent to about 3 percent by weight of the carrier.

10. A method of increasing the rate of healing of a wound in a patient having a wound comprising topically applying to the wound a pharmaceutically acceptable carrier containing an effective amount of acetaminophen to increase the rate of healing of the wound, said acetaminophen being applied in divided doses.

11. The method of claim 10, wherein the doses are applied from one to eight times daily and the acetaminophen is present in the range of from about 0.05 percent to about 10 percent by weight of the carrier.

12. The method of claim 11, wherein the pharmaceutically acceptable carrier is an ointment or cream.

13. The method of claim 11, wherein the pharmaceutically acceptable carrier is an aqueous solution.

14. The method of claim 11, wherein the pharmaceutically acceptable carrier contains alcohol.

15. The method of claim 11, wherein the acetaminophen is present in an amount not less than 0.05 percent by weight of the carrier.

16. The method of claim 11, wherein the acetaminophen is present in the range of from about 0.05 percent to about 3 percent by weight of the carrier.

* * * * *